(12) United States Patent
Yilmaz

(10) Patent No.: US 12,274,828 B2
(45) Date of Patent: Apr. 15, 2025

(54) MOUTHPIECE

(71) Applicant: Hakan Yilmaz, Seattle, WA (US)

(72) Inventor: Hakan Yilmaz, Seattle, WA (US)

( * ) Notice: Subject to any disclaimer, the term of this patent is extended or adjusted under 35 U.S.C. 154(b) by 1139 days.

(21) Appl. No.: 16/934,191

(22) Filed: Jul. 21, 2020

(65) Prior Publication Data
US 2022/0023564 A1    Jan. 27, 2022

(51) Int. Cl.
*A61M 16/04*    (2006.01)

(52) U.S. Cl.
CPC .... *A61M 16/0493* (2014.02); *A61M 16/0497* (2013.01)

(58) Field of Classification Search
CPC ...................................................... A61B 1/32
See application file for complete search history.

(56) References Cited

U.S. PATENT DOCUMENTS

| | | | | |
|---|---|---|---|---|
| 569,839 | A * | 10/1896 | Roeloffs | A61B 17/02 600/219 |
| 815,907 | A * | 3/1906 | a | A61B 1/32 600/203 |
| 1,025,265 | A * | 5/1912 | a | A61B 17/0206 600/242 |
| 1,798,194 | A | 3/1931 | Dodge | |
| 2,002,021 | A * | 5/1935 | Rouse | A61B 17/6408 606/86 R |
| 2,481,007 | A * | 9/1949 | Dugdale | A01K 97/18 43/53.5 |
| 2,670,731 | A * | 3/1954 | Zoll | A61B 17/0206 600/234 |
| 2,969,059 | A | 1/1961 | Meek | |
| 3,509,873 | A * | 5/1970 | Karlin | A61B 17/02 600/231 |
| 3,707,800 | A * | 1/1973 | Wolfe | A01K 97/18 43/53.5 |
| 3,813,096 | A | 5/1974 | Welch | |
| 4,151,837 | A | 5/1979 | Millard et al. | |
| 4,883,046 | A * | 11/1989 | Fontenot | A61H 1/02 482/901 |

(Continued)

FOREIGN PATENT DOCUMENTS

EP    3 476 274 A1    5/2019

OTHER PUBLICATIONS

Tenda Market, "Comfort Desk Pro—Adjustable Laptop Stand", <www.tendamarkets.co/products/comfort-desk-pro-adjustable-laptop-stand>, 2020, 15 pages.

(Continued)

*Primary Examiner* — LaToya M Louis
(74) *Attorney, Agent, or Firm* — Foley & Lardner LLP

(57) ABSTRACT

An apparatus includes an outer portion including a primary opening, a first pillar support and a second pillar support coupled to the outer portion, a first upper gum support rotatably coupled to the first pillar, a first lower gum support rotatably coupled to the first pillar, a second upper gum support rotatably coupled to the second pillar, a second lower gum support rotatably coupled to the second pillar, a first upper gum end rotatably coupled to the first upper gum support, a first lower gum end rotatably coupled to the first lower gum support, a second upper gum end rotatably coupled to the second upper gum support, and a second lower gum end rotatably coupled to the second lower gum support.

20 Claims, 6 Drawing Sheets

(56) References Cited

U.S. PATENT DOCUMENTS

| | | | | |
|---|---|---|---|---|
| 4,909,502 | A | * | 3/1990 | Beeuwkes, III ..... A63B 23/032 482/11 |
| 4,955,367 | A | * | 9/1990 | Homsy ................... A61H 1/02 433/215 |
| 5,062,191 | A | * | 11/1991 | Carr ...................... B25B 27/205 29/268 |
| 5,097,820 | A | * | 3/1992 | Shulman ................. A61B 1/24 600/237 |
| 5,176,594 | A | * | 1/1993 | Lee ......................... A61H 1/02 482/148 |
| 5,527,261 | A | | 6/1996 | Monroe et al. |
| 5,570,704 | A | | 11/1996 | Buzzard et al. |
| 5,931,777 | A | * | 8/1999 | Sava ...................... A61B 17/02 600/210 |
| 6,116,580 | A | | 9/2000 | Hull |
| 6,413,231 | B1 | * | 7/2002 | Berman ................... A61H 1/02 482/11 |
| 6,558,392 | B1 | * | 5/2003 | Martini ................ A61B 17/025 606/208 |
| 6,708,587 | B1 | * | 3/2004 | Noniewicz ............... B25B 5/06 81/319 |
| 7,438,667 | B2 | * | 10/2008 | Robbins ............. A63B 21/0004 482/122 |
| 7,887,461 | B2 | * | 2/2011 | Bakhtiyari ........... A63B 23/032 482/127 |
| 8,702,569 | B2 | | 4/2014 | Martin et al. |
| 8,753,348 | B2 | * | 6/2014 | DiDomenico ..... A61B 17/8004 606/105 |
| 9,867,753 | B2 | * | 1/2018 | Garay-Arauz ........... A61H 1/02 |
| 10,086,228 | B2 | * | 10/2018 | Yoshitake .............. A63B 23/03 |
| 10,441,260 | B2 | * | 10/2019 | Wu ........................ A61B 17/02 |
| 11,109,753 | B2 | * | 9/2021 | Weiman ............. A61B 17/3421 |
| 11,596,299 | B2 | * | 3/2023 | Mantovani ............. A61B 13/00 |
| 2003/0080485 | A1 | * | 5/2003 | Lo ............................. F16B 2/12 269/6 |
| 2003/0088158 | A1 | * | 5/2003 | Chien .................. A63B 23/032 600/237 |
| 2005/0211024 | A1 | * | 9/2005 | Shpakow ............ G01M 3/3272 81/3.43 |
| 2007/0012319 | A1 | * | 1/2007 | Frascati ............... A63B 23/032 128/861 |
| 2007/0089752 | A1 | * | 4/2007 | Christensen, III ... A63B 23/032 128/845 |
| 2007/0287598 | A1 | * | 12/2007 | Christensen, III ....... A61H 1/02 482/11 |
| 2008/0201324 | A1 | | 8/2008 | Aronowich et al. |
| 2008/0264216 | A1 | * | 10/2008 | Duffy ....................... B25B 7/14 81/319 |
| 2010/0011916 | A1 | * | 1/2010 | Christensen, III ........ B25B 7/12 81/342 |
| 2010/0086889 | A1 | * | 4/2010 | Lindquist ................. A61C 7/04 433/4 |
| 2013/0098372 | A1 | | 4/2013 | Webster et al. |
| 2013/0123581 | A1 | * | 5/2013 | Fritzinger ................ A61B 1/32 600/201 |
| 2013/0204090 | A1 | * | 8/2013 | Blain ................... A61B 17/025 600/213 |
| 2014/0238410 | A1 | | 8/2014 | Goldsby |
| 2016/0058275 | A1 | * | 3/2016 | Hu .......................... A61B 1/32 433/140 |
| 2017/0273550 | A1 | * | 9/2017 | Wu ........................ A61B 17/02 |
| 2018/0085274 | A1 | * | 3/2018 | Lee ......................... A61B 1/32 |
| 2021/0228072 | A1 | * | 7/2021 | Van Abel ................ A61B 1/32 |

OTHER PUBLICATIONS

Non-Final Office Action on U.S. Appl. No. 17/385,170 dated Mar. 2, 2022.

* cited by examiner

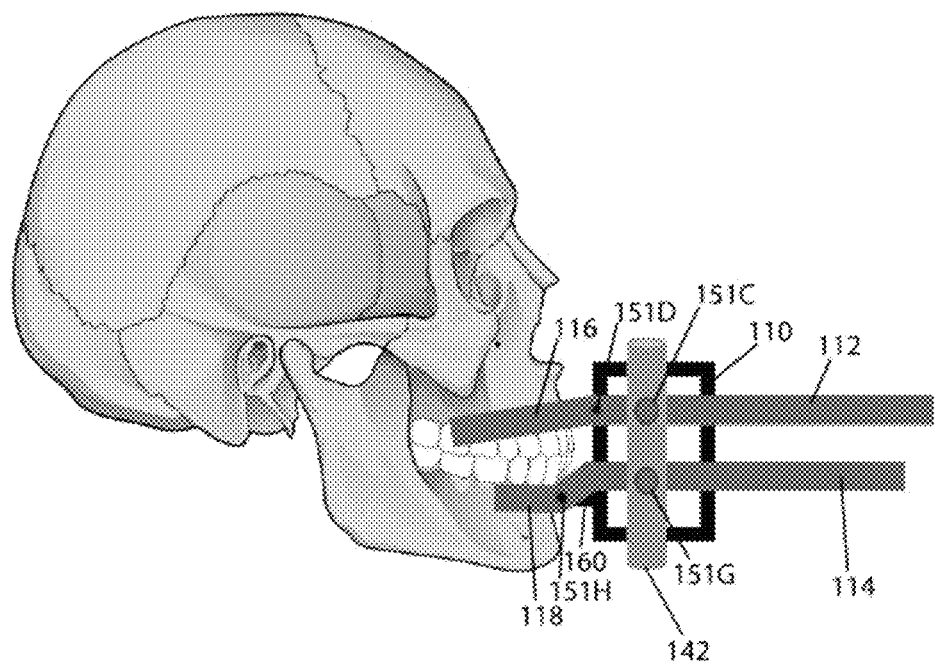
FIG. 3A
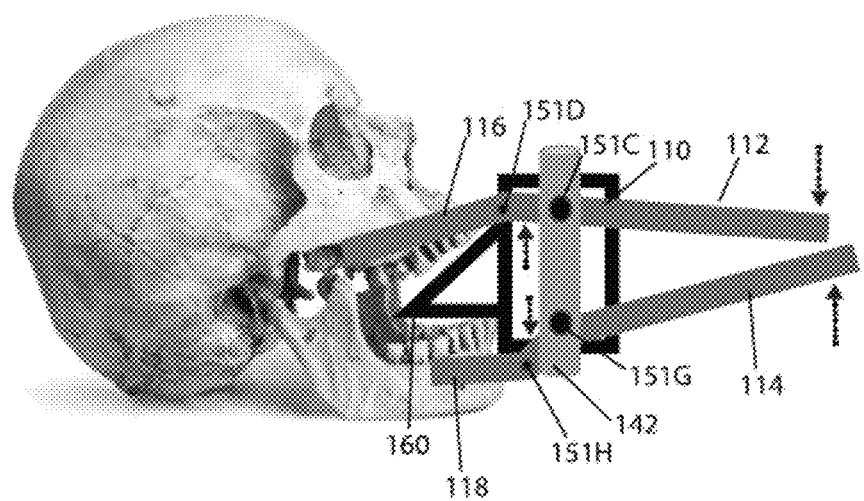
FIG. 3B
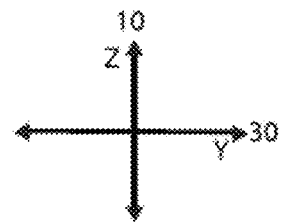

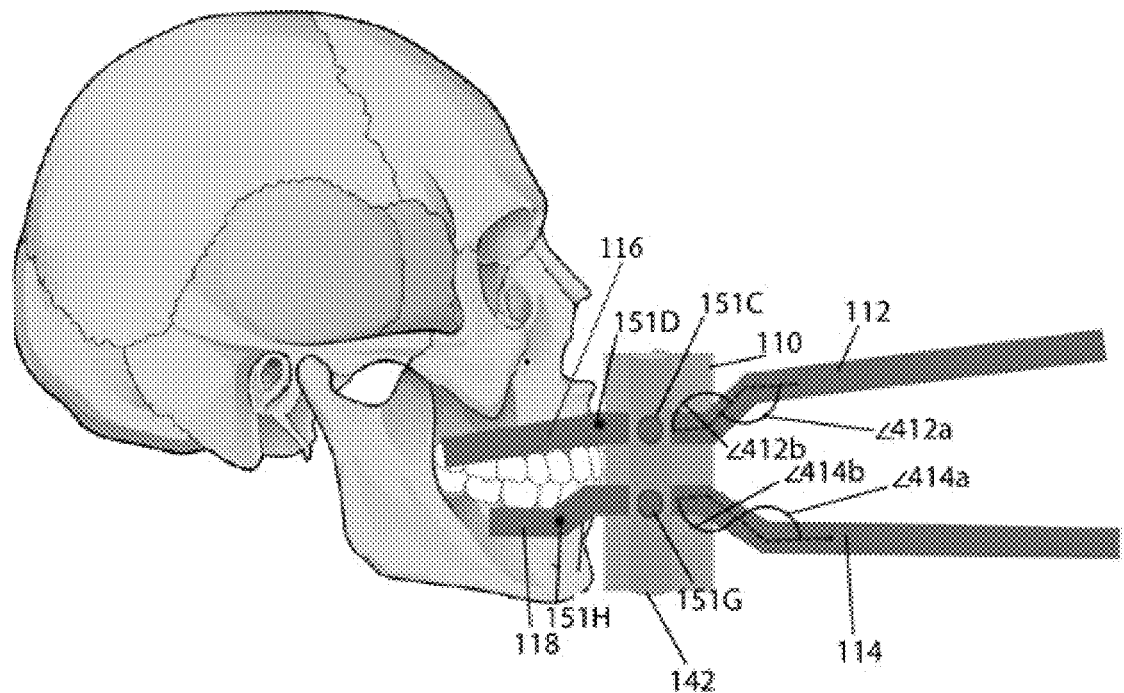
FIG. 4
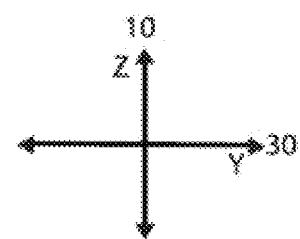

MOUTHPIECE

BACKGROUND

The present invention relates generally to medical devices for respiratory aid.

Hospital patients may require use of a breathing tube (i.e., a tracheal tube) in order to assist with the breathing process. Breathing tubes are commonly used when a patient is undergoing general anesthesia during a surgical procedure. Breathing tubes may also be used in emergency situations, such as when the patient is experiencing severe respiratory problems. In use, a breathing tube may be inserted through a patient's mouth and into the trachea, thereby creating a passageway to the patient's lungs to facilitating the exchange of oxygen and carbon dioxide that might otherwise be diminished or prevented.

SUMMARY

One embodiment relates to an apparatus including an outer portion that includes a primary opening defined by an inner surface of the outer portion, a first pillar support coupled to a first lateral side of the outer portion, wherein the first pillar support is configured to receive a first pillar such that the first pillar may rotate within the first pillar support, a second pillar support coupled to a second lateral side of the outer portion, the second lateral side being opposite of the first lateral side, wherein the second pillar support is configured to receive a second pillar such that the second pillar may rotate within the second pillar support, a first upper gum support rotatably coupled to the first pillar, a first lower gum support rotatably coupled to the first pillar, a second upper gum support rotatably coupled to the second pillar, a second lower gum support rotatably coupled to the second pillar, a first upper gum end rotatably coupled to the first upper gum support, wherein the first upper gum end is configured to be received by an upper portion of a mouth, a first lower gum end rotatably coupled to the first lower gum support, wherein the first lower gum support is configured to be received by a lower portion of the mouth, a second upper gum end rotatably coupled to the second upper gum support, wherein the second upper gum end is configured to be received by the upper portion of the mouth, and a second lower gum end rotatably coupled to the second lower gum support, wherein the second lower gum end is configured to be received by the lower portion of the mouth.

Another embodiment relates to a method of opening a mouth using a mouthpiece. The method includes inserting a first upper gum end into the mouth, wherein the first upper gum end is received by a first lateral side of an upper portion of the mouth, inserting a second upper gum end into the mouth, wherein the second upper gum end is received by a second lateral side of the upper portion of the mouth, the second lateral side being opposite the first lateral side, inserting a first lower gum end into the mouth, wherein the first lower gum end is received by the first lateral side of a lower portion of the mouth, inserting a second lower gum end into the mouth, wherein the second lower gum end is received by the second lateral side of the lower portion of the mouth, applying a separating force to a first upper gum support, wherein the first upper gum support is rotatably fixed to a first pillar and rotatably fixed to the first upper gum end, applying a separating force to a second upper gum support, wherein the second upper gum support is rotatably fixed to a second pillar and rotatably fixed to the second upper gum end, applying a separating force to a first lower gum support, wherein the first lower gum support is rotatably fixed to the first pillar and rotatably fixed to the first lower gum end, and applying a separating force to a second lower gum support, wherein the second lower gum support is rotatably fixed to the second pillar and rotatably fixed to the second lower gum end. The first pillar and the second pillar are coupled to an outer portion comprising a primary opening defined by an inner surface of the outer portion. Applying the separating force to the first upper gum support and the first lower gum support causes the first upper gum end and the second upper gum end to move away from each other, and applying the separating force to the second upper gum support and the second lower gum support causes the second upper gum end and the second lower gum end to move away from each other.

Another embodiment relates to an apparatus including an outer portion configured to be positioned outside of a mouth, an inner wedge configured to be at least partially inserted into the mouth, wherein the inner wedge is positioned within an opening in the outer portion, a first upper gum end coupled to the outer portion and configured to be received by an upper portion of the mouth, a first lower gum end coupled to the outer portion and configured to be received by a lower portion of the mouth, a second upper gum end coupled to the outer portion and configured to be received by the upper portion of the mouth, and a second lower gum end coupled to the outer portion and configured to be received by the lower portion of the mouth.

These and other features, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 3A is a side view of the mouthpiece of FIG. 1 in a disengaged position and in relation to a human skull, according to an exemplary embodiment.

FIG. 3B is a side view of the mouthpiece of FIG. 1 in an engaged position and in relation to a human skull, according to an exemplary embodiment.

FIG. 4 is a side view of the mouthpiece of FIG. 1 in a disengaged position and in relation to a human skull, according to an exemplary embodiment.

DETAILED DESCRIPTION

Figure 1:
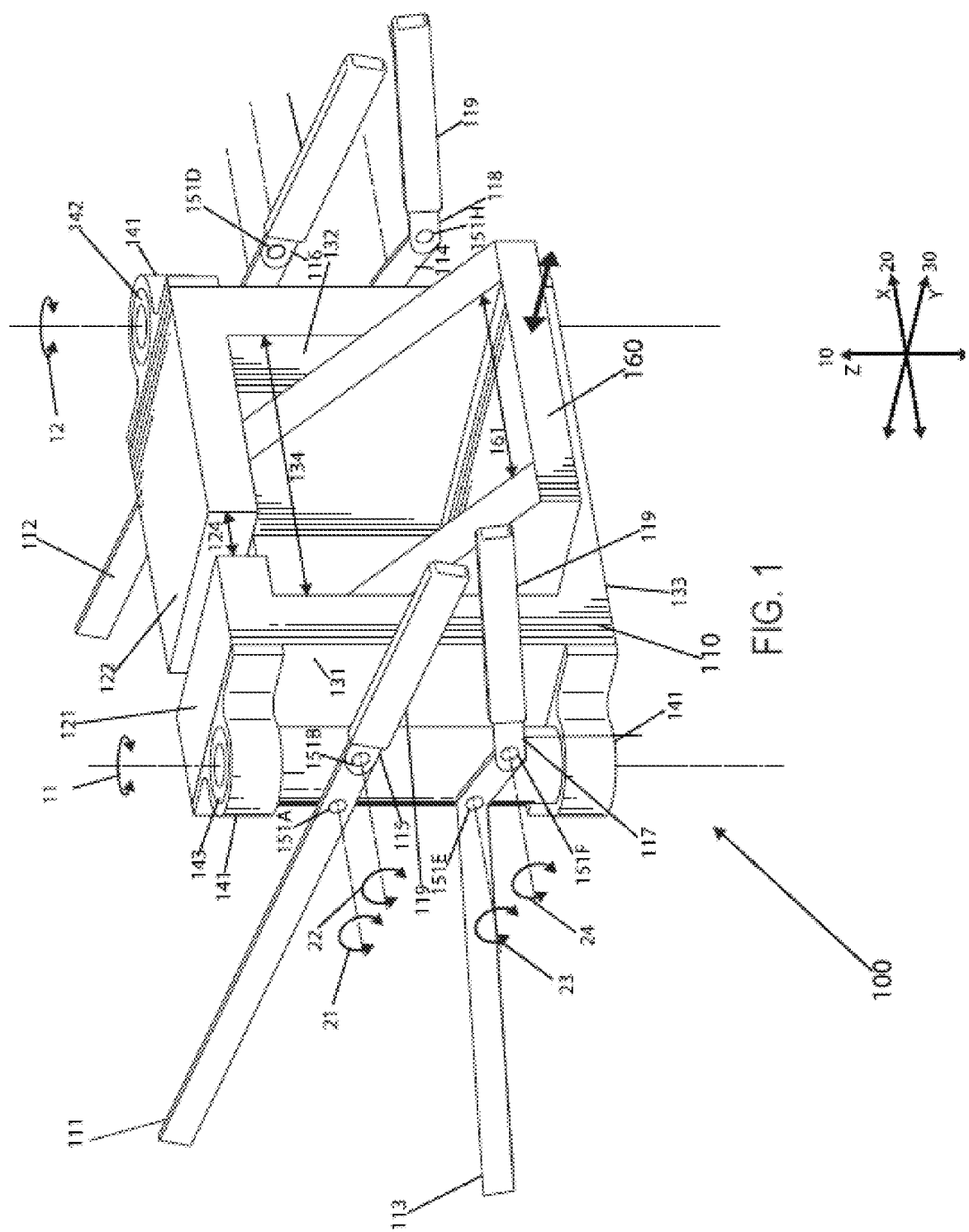
FIG. 1 is a perspective view of a mouthpiece, according to an exemplary embodiment.

The act of inserting the breathing tube into a patient's mouth and into the patient's trachea is referred to as endotracheal intubation. Once the patient is prepared for the endotracheal intubation, which might mean that the patient is unconscious due to anesthesia that has been administered, a doctor may use an instrument called a laryngoscope to perform the endotracheal intubation. A laryngoscope is a device that consists of a handle and a dull blade that guides the endotracheal breathing tube to its proper position in the trachea.

Tilting the patient's head back slightly, the doctor will insert the laryngoscope through the patient's mouth and down into their throat. The doctor may need to take special care to avoid the patient's teeth when inserting the laryngoscope. Once the laryngoscope is positioned within in the patient's throat, the doctor may use the laryngoscope's blade to gently raise the patient's epiglottis, which is a flap of tissue that protects the patient's larynx. The doctor may then advance the tip of the endotracheal breathing tube into the patient's trachea, and inflate a small balloon that surrounds the tube to ensure that the tube remains in place. Once the endotracheal breathing tube is properly positioned within the patient, the doctor may remove the laryngoscope and the external portion of the endotracheal breathing tube may be secured (e.g., taped) to the side of the patient's mouth.

In certain situations, patient's mouth may be shut, thereby making it more difficult to insert the endotracheal breathing tube. For example, if a patient is having a seizure (e.g., an epileptic seizure), the patients law may lock (i.e., the patients jaw muscles contract, thereby making it difficult to open the patients mouth). Particularly when a patient is seizing, which can itself be the source of respiratory problems, the muscles around the patient's mouth tighten and prevent their mouth from opening without a great external force. In these cases, it is necessary to provide such an external force but without interacting with the patient's teeth directly in order to avoid permanent damage. In this situation, a patient's jaw mat be forcibly opened by the doctor or other individual, however, this may put the safety of the patient and the doctor or other individual in danger. For example, the patient's teeth may be damaged while the patient's jaw is being force opened. Further, the doctor or other individual that is forcing the patient's jaw open may injure their hand and/or fingers while forcibly holding the patient's jaw open.

The mouthpiece disclosed in the present application may be coupled to the patient's jaw and a separating force may be applied to the mouthpiece to creating an opening force to the patient's mouth. For example, the mouthpiece may couple to the outside of the patient's gums. By attaching to a patient's gums, the mouthpiece is not only avoiding contact with sensitive teeth but also reducing the amount of force required to open the patient's jaws, as gums may be more easily manipulated in such a situation. In some embodiments, the mouthpiece is also fitted with a groove or hole that serves to guide an endotracheal breathing tube, enabling the mouthpiece to not only open the patient's mouth but also protect the patient's teeth from further damage as the laryngoscope is inserted into the patient's mouth to guide the breathing tube into place.

In some embodiments, gum separators may be used to couple the mouthpiece to the patient's jaw. For example, the gum separators may be fitted with easily removable caps or sheathes (e.g., sanitary caps) that make contact with the patient's gums. In this embodiment, the caps can be cleaned or disposed of and replaced without much difficulty, ensuring that the device itself can be used repeatedly. The caps may also protect the patient's gums from coming directly in contact with the gum separators, which, in some embodiments, may be made of metal or a similarly rigid material.

The caps may be made of any combination of silicone, rubber, and/or any other material approved for use in medical devices, such as ABS, acetal copolymer, delrin, PET-P, flurosint, halar, hydex, kynar, noryl, nylon, PEEK, polycarbonate, polyethlyenes (e.g. LDPE, HDPE, and UHMW), polypropylene homopolymer, PPSU, PSU, radel A, radel R, and Rulon 641.

Referring to FIG. 1, a mouthpiece 100 is shown, according to an example embodiment. As pictured, the mouthpiece 100 includes an outer portion 110 and an inner wedge 160. The inner wedge 160 may be generally wedge shaped. The outer portion 110 may include a first side panel 131, a second side panel 132, a first upper panel 121, a second upper panel 122, and a lower panel 133. As pictured, the first side panel 131 is disposed longitudinally opposite from the second side panel 132 along an x-axis 20. The first upper panel 121 and the second upper panel 122, may be coplanar (e.g. adjacent to laterally, in line with, etc.) within a first plane. The first plane may be parallel to the plane formed by the x-axis 20 and the y axis 30. Further, the first upper panel 121 and the second upper panel 122 may be disposed axially away from the lower panel 133. For example, the lower panel 133 may be positioned lower along a z-axis 10. The surface of the lower panel 133 may form a second plane. In certain embodiments, the second plane is parallel to the first plane.

The outer portion 110 may also include a plurality of pillar supports 141. The pillar supports may be configured to receive a pillar (e.g., a first pillar 143 and a second pillar 142). The first pillar 143 may be fixed to the first side panel 131 by two pillar supports 141 such that the first pillar 143 is oriented along the z-axis 10. The first pillar 143 may be configured to rotate about the z-axis 10, as shown by the arrows 11 in FIG. 1. The second pillar 142 may be fixed to the second side panel 132 by two pillar supports 141 such that the second pillar 142 is oriented along the z-axis 10 and is capable of rotation around the z-axis, as shown by the arrows 12 in FIG. 1.

The outer portion 110 may also include a plurality of gum supports. For example, the outer portion may 110 may include a first upper gum support 111, a second upper gum support 112, a first lower gum support 113, and a second lower gum support 114. In the example embodiment shown, the first upper gum support 111 and the first lower gum support 113 are rotationally fixed to the first pillar 143 via rotator pins 151A and 151E respectively, such that the first upper gum support 111 and the first lower gum support 113 are able to rotate around the rotator pins 151A and 151E respectively, as shown by the arrows 21 and 23 in FIG. 1. The second upper gum support 112 and the second lower gum support 114 may be rotationally fixed to the second pillar 142 via rotator pins 151C and 151H respectively, such that the second upper gum support 112 and the second lower gum support 114 are able to rotate around the rotator pins 151C and 151H respectively.

The first upper gum support 111 extends substantially laterally from the first pillar 143 along a y-axis 30, although the exact angle of extension is variable due to possible rotation by the first pillar 143 and around the rotation pin 151A. The first upper gum support 111 includes a first upper gum end 115 that is rotationally fixed to the first upper gum support 111 by a rotator pin 151B, such that the first upper gum end 115 is able to rotate around the rotator pin 151B, as shown by the arrows 22 in FIG. 1 but otherwise remains in the same alignment with the first upper gum support 111 (i.e. the first upper gum support 111 and the first upper gum end are fixed to each about the other axes). The second upper gum support 112 may be similar to the first upper gum support 111. For example, the second upper gum support 112 extends substantially laterally from the second pillar 142 along the y-axis 30, although the exact angle of extension is variable due to possible rotation by the second pillar 142 and around the rotator pin 151C. The second upper gum support 112 includes a second upper gum end 116 that is rotationally fixed to the second upper gum support 112 by a rotator pin 151D, such that the second upper gum end 116 is able to rotate around the rotator pin 151D, as shown in FIG. 1 but otherwise remains in the same alignment with the second upper gum support 112 (i.e. the second upper gum support 112 and the second upper gum end 116 are fixed to each about the other axes).

In certain embodiments, the first upper gum end 115 is configured to be received by a upper portion of a patient's mouth (e.g., the upper gum line, the upper cheek area, the upper row of teeth, etc.), as is discussed in greater detail below. For example, the first upper gum end 115 may be configured to be received by a first lateral side (e.g., the left side of the patient's mouth) of the upper portion of the patient's mouth. Further, the second upper gum end 116 may be configured to be received by the upper portion of a patient's mouth (e.g., the upper gum line, the upper cheek area, the upper row of teeth, etc.), as is discussed in greater detail below. For example, the second upper gum end 116 may be configured to be received by a second lateral side (e.g., the right side of the patient's mouth) of the upper portion of the patient's mouth. Furthermore, the first lower gum end 117 may be configured to be received by a lower portion of a patient's mouth (e.g., the lower gum line, the lower cheek area, the lower row of teeth, etc.), as is discussed in greater detail below. For example, the first lower gum end 117 may be configured to be received by a first lateral side (e.g., the left side of the patient's mouth) of the lower portion of the patient's mouth. Furthermore, the second lower gum end 118 may be configured to be received by a lower portion of a patient's mouth (e.g., the lower gum line, the lower cheek area, the lower row of teeth, etc.), as is discussed in greater detail below. For example, the second lower gum end 118 may be configured to be received by a second lateral side (e.g., the right side of the patient's mouth) of the lower portion of the patient's mouth.

The first lower gum support 113 extends substantially laterally from the first pillar 143 along a y-axis 30, although the exact angle of extension is variable due to possible rotation by the first pillar 143 and around the rotation pin 151E. The first lower gum support 113 includes a first lower gum end 117 that is rotationally fixed to the first lower gum support 113 by a rotator pin 151F, such that the first lower gum end 117 is able to rotate around the rotator pin 151F, as shown by the arrows 24 in FIG. 1 but otherwise remains in the same alignment with the first lower gum support 113 (i.e. the first lower gum support 113 and the first lower gum end 117 are fixed to each about the other axes). The second lower gum support 114 may be similar to the first lower gum support 113. For example, the second lower gum support 114 extends substantially laterally from the second pillar 142 along the y-axis 30, although the exact angle of extension is variable due to possible rotation by the second pillar 142 and around the rotator pin 151G. The second lower gum support 114 includes a second lower gum end 118 that is rotationally fixed to the second lower gum support 114 by a rotator pin 151H, such that the second lower gum end 118 is able to rotate around the rotator pin 151H, as in FIG. 1 but otherwise remains in the same alignment with the second lower gum support 114 (i.e. the second lower gum support 114 and the second lower gum end 118 are fixed to each about the other axes).

Each of the first upper gum end 115, the first lower gum end 117, the second upper gum end 116, and the second lower gum end 118 (collectively, the gum ends 115-118) include one of a plurality of sanitary caps 119 each of which is removably coupled to the end of the respective the gum ends 115-118 that is opposite of the rotator pin 151. The plurality of sanitary caps 119 are structured to completely cover the tip of the gum ends 115-118 such as to prevent the gum ends 115-118 from making direct contact with the patient. In this way, the plurality of sanitary caps 119 provide a quick and easy method to clean and re-use the mouthpiece 100 between patients. Because the plurality of sanitary caps 119 are the only part of the mouthpiece 100 that makes direct contact with the patient and the plurality of sanitary caps 119 are removably coupled to the gum ends 115-118, every component of the mouthpiece 100 that makes direct contact with the patient is able to be removed and either cleaned or replaced in between uses. Further, the plurality of sanitary caps 119 may be made from a less rigid material than the gum ends, thereby providing a cushion between the gum ends 115-118, which in some embodiments are constructed of a rigid material, and the patient.

In this exemplary embodiment, both the first lower gum support 113 and the second lower gum support 114 include a slight angle immediately prior to the connecting point, which, when combined with the possible rotation of the first lower gum end 117 and the second lower gum end 118 respectively, enables a more ergonomic fit with a patient's mouth by aligning the parts of the mouthpiece 100 that actually make contact to the patient's gums with the natural gum line. In certain embodiments, the slight angle may range between 120-150° as formed by the two portions of the first lower gum support 113 (forming angle ∠113) and the second lower gum support 114 (forming angle ∠114) on either side of the rotator pin 151, with the rotator pin 151 defined as a vertex of the angle.

The outer portion 110 may also include an outer primary opening 134 and a secondary opening 124. The primary opening 134 is the space created longitudinally between the first side panel 131 and the second side panel 132 and axially between the first upper panel 121, the second upper panel 122, and the lower panel 133. The secondary opening 124 is the space created longitudinally between the first upper panel 121 and the second upper panel 122. The outer primary opening 134 may be large enough to accommodate a laryngoscope and breathing tube, such that a user doctor has enough space to properly move and manipulate the laryngoscope to ensure proper placement of the breathing tube. The secondary opening 124 is large enough to accommodate the laryngoscope such that the user doctor is able to disengage the laryngoscope from the breathing tube and remove the laryngoscope from the patient's mouth without disrupting the newly-placed breathing tube.

The outer primary opening 134 may be configured to receive the inner wedge 160, such that the inner wedge 160 fits snugly (e.g., the inner wedge 160 is in contact with the outer portion 110) within the outer portion 110. In some embodiments, this snug fit is a friction fit, such that the inner wedge 160 is held in place within the outer portion 110 by the friction force generated by interacting surfaces of the inner wedge 160 and the outer portion 110. The inner wedge 160 is shown in greater detail in FIG. 2, as is discussed below.

Figure 2:
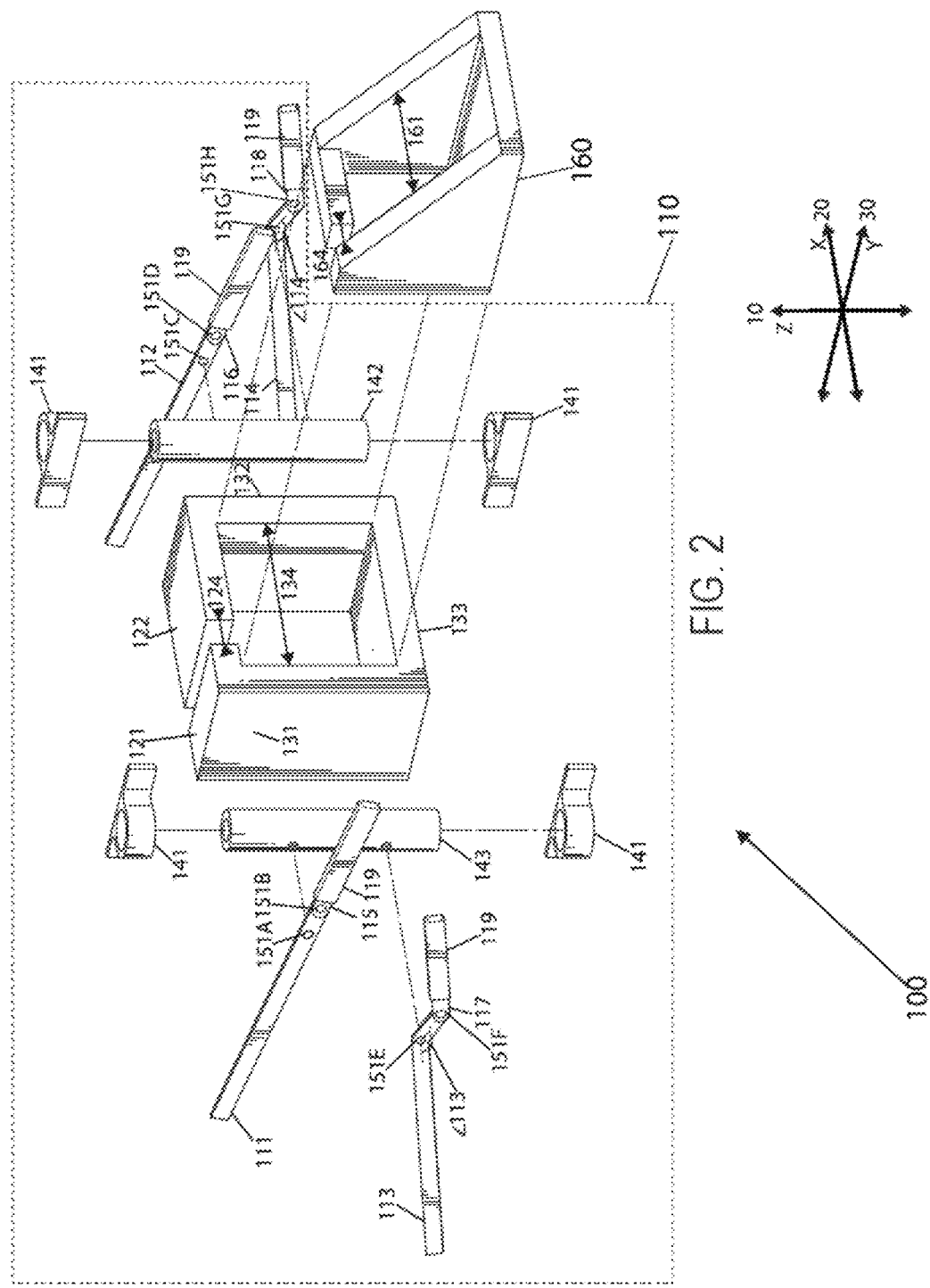
FIG. 2 is an exploded view of the mouthpiece of FIG. 1, according to an exemplary embodiment.

Referring now to FIG. 2, an exploded view of the mouthpiece 100 is shown according to an example embodiment. The mouthpiece 100 may include an inner wedge 160 that includes a wedge secondary opening 164. In certain embodiments, the secondary opening 164 may be the same size as the corresponding secondary opening 124 in the outer portion. The inner wedge 160 may also include an inner primary opening 161. In certain embodiments, the wedge secondary opening 164 may be smaller than the inner primary opening 161. The primary opening 134 may be larger than the outer size of the inner wedge 160. The inner primary opening 161 may be smaller than the primary opening 134 less twice the thickness of the edge sidewalls of the inner wedge 160. In some embodiments, the inner primary opening 161, despite being smaller than the outer primary opening 134, may be large enough to accommodate a laryngoscope and breathing tube, such that a user doctor has enough space to properly move and manipulate the laryngoscope to ensure proper placement of the breathing tube. The inner wedge 160 may be structured to be pushed along the y-axis 30 and into the patient once the separating force has been applied in order to prop the patient's jaw open, enabling removal of the outer portion 110 without causing the object to return to its prior closed state in which air flow was restricted.

In use, the mouthpiece 100 may be used to create a separating force (e.g., an opening force) to open a patient's jaw. For example, a doctor or other user of the mouthpiece 100 may use the first upper gum support 111, the second upper gum support 112, the first lower gum support 113, and the second lower gum support 114 (collectively, the gum supports 111-114) to create the separating force. In an example embodiment, the gum supports 111-114 are fit to the object requiring the separating force (e.g., the patient's gums, mouth, teeth, jaw, cheeks, etc.). The gum supports 111-114 may be adjusted to fit a specific patient by rotating the gum supports 111-114 about the rotator pins 151 connected to the first pillar 143 and the second pillar 142 and rotating the gum ends 115-118 about the plurality of rotator pins 151 connected to the gum supports 111-114. Once the gum supports 111-114 are in a desired orientation, the gum supports 111-114 are tightened onto the objecting requiring the separating force (e.g., the patient's gums, mouth, teeth, jaw, cheeks, etc.) by rotating the first pillar 143 and the second pillar 142 in the plurality of pillar supports 141. Once tightened, a compressing force along the z-axis 10 is applied to the ends of the first upper gum support 111 and the first lower gum support 113 opposite the plurality of sanitary caps 119, and a compressing force along the z-axis 10 is applied to ends of the second upper gum support 112 and the second lower gum support 114 that are opposite the plurality of sanitary caps 119. For example, a compressing force may be applied by a doctor or other operator of the mouthpiece 100. Further, the mouthpiece 100 may be connected to a motor, or multiple motors, that may creating a compressing force. When the compressing forces are applied, the plurality of sanitary caps 119 move in the opposite direction of the compressing forces along the z-axis 10, such that the separating force is applied to the desired object and airflow through the object is enabled.

Referring now to FIGS. 3A and 3B, the mouthpiece 100 is shown according to an example embodiment. In this exemplary embodiment, the object is a human skull. As shown in FIG. 3A, the mouthpiece 100 is shown interacting with the human skull via the second upper gum end 116 and the second lower gum end 118 in contact with the human skull directly above a top row of teeth and below a bottom row of teeth, respectively. The second upper gum end 116 and the second lower gum end 118 may be rotated around the rotator pins 151D and 151H respectively in order to be properly positioned on the gum lines of the human skull. Although not shown in FIG. 3A, any action performed on or function performed by the second upper gum end 116 and the second lower gum end 118 may also be performed on or by the first upper gum end 115 and the first lower gum end 117 respectively. As such, the second upper gum end 116 and the second lower gum end 118 interact with the human skull at a gum line of the human skull. Once the second upper gum end 116 and the second lower gum end 118 are in place, the rotating force around the second pillar 142 is applied to the second upper gum support 112 and the second lower gum support 114, tightening the second upper gum end 116 and the second lower gum end 118 onto the gum line of the human skull.

It should be appreciated that, in certain embodiments, the first upper gum support 111 and the first upper gum end 115 may be one rigidly fixed piece (i.e., the first upper gum support 111 is not rotatably fixed to the first upper gum end 115, but is instead rotatably fixed to the first upper gum end 115). For example, the first upper gum support 111 and the first upper gum end 115 may be manufactured as a single. Further, the second upper gum support 112 and the second upper gum end 116 may be one rigidly fixed piece. Furthermore, the first lower gum support 113 and the first lower gum end 117 may be one rigidly fixed piece. Furthermore, the second lower gum support 114 and the second lower gum end 118 may be one rigidly fixed piece.

As shown in FIG. 3B, the mouthpiece 100 may be manipulated such that the mouthpiece 100 is in an enabled position following application of the separating force. As shown, one end of the second upper gum support 112 and one end of second lower gum support 114 are moved closer together along the z-axis 10 (as shown by dashed arrows). Rotation of the second upper gum support 112 and the second lower gum support 114 around the rotator pins 151C and 151G moves the opposite ends of the second upper gum support 112 and the second lower gum support 114 apart along the z-axis 10 (as shown by the dashed arrows), which, in turn, separates the second upper gum end 116 and the second lower gum end 118 along the z-axis 10. Because the second upper gum end 116 and the second lower gum end 118 are tightly fit to the gum lines of the human skull, the separating force applied to the second upper gum end 116 and the second lower gum end 118 is transferred in equal quantity to the human skull, thereby separating a lower jaw of the human skull from an upper jaw of the human skull, along the z-axis 10. Once the jaws have been separated, the inner wedge 160 may be pushed from a receded position shown in FIG. 3A into the space between the upper jaw and the lower jaw as shown in FIG. 3B.

Referring now to FIG. 4, the mouthpiece 100 is shown in a disengaged orientation according to another example embodiment. As shown in FIG. 4, in some embodiments, both the second upper gum support 112 and the second lower gum support 114 include a set of slight angles prior to the connecting point with the second pillar 142, which enables a more ergonomic fit for an operating user (e.g., a doctor, nurse, etc.) by giving more room for the separating force to be applied to the gum supports 111-114. In certain embodiments, the set of slight angles includes two separate angles for each gum support 111-114: as shown in FIG. 4, the second upper gum support 112 includes angles ∠412A and ∠412B, while the second lower gum support 114 includes angles ∠414A and ∠414B. In certain embodiments, angles ∠412A-B and ∠414A-B may range from 120-150° formed by portions of the second upper gum support 112 (forming angles ∠412A-B) and the second lower gum support 114 (forming angles ∠414A-B).

In some of these embodiments, the gum ends 115-118 make direct contact with the gum lines of the human skull. In other of these embodiments, each of the gum ends 115-118 includes at least one of the plurality of sanitary caps 119, such that the plurality of sanitary caps are the only components of the mouthpiece in direct contact with the human skull. In these embodiments with the plurality of sanitary caps 119, the sanitary caps are removably coupled to an end of the gum ends 115-118 as shown in FIGS. 1 and 2.

Figure 5A:
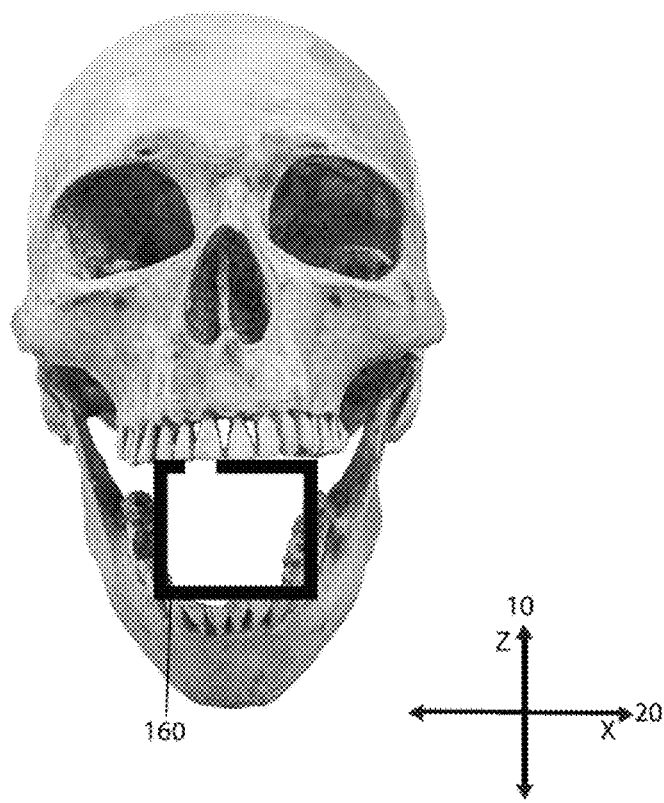
FIG. 5A is a front view of an inner wedge of the mouthpiece of FIG. 1 in relation to a human skull, according to an exemplary embodiment.
Figure 5B:
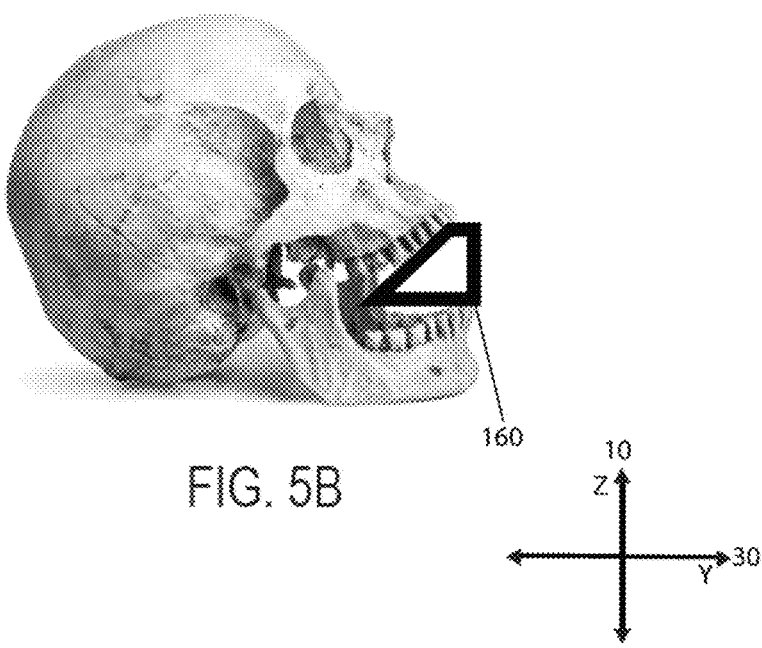
FIG. 5B is a side view of an inner wedge of the mouthpiece of FIG. 1 in relation to a human skull, according to an exemplary embodiment.

In some embodiments, once the inner wedge 160 is in position (i.e. between the upper jaw and the lower jaw), the second upper gum end 116 and the second lower gum end 118 are loosened from the gum lines of the human skull (a process described in greater depth below). Because the second upper gum end 116 and the second lower gum end 118 are no longer in contact with the gum lines of the human skull, the separating force being transferred to the human skull via the second upper gum end 116 and the second lower gum end 118 are no longer transferred. As such, the upper jaw and the lower jaw may rest on the inner wedge 160 (i.e., the upper angled surface of the inner wedge may be in contact with the upper portion of the patient's mouth and the lower flat surface may be in contact with the lower portion of the patient's mouth), thereby keeping the jaw in an open orientation. In some of these embodiments, the outer portion 110 may then be removed, which is discussed in greater detail in FIGS. 5A and 5B.

Once the mouthpiece 100 is positioned within a desired location, an operator of the mouthpiece may secure the gum supports 111-114 to prevent the gum supports 111-114 from undesirably shifting. For example, in some embodiments, the gum supports 111-114 and associated components are restricted in movement because the rotator pins 151, the first pillar 143, the second pillar 142, and the plurality of pillar supports 141 are structured such that the force required to cause rotation of the first pillar 143 or the second pillar 142 or rotation of any component around the rotator pins 151 (i.e. inertia) is greater than is supplied by the natural resistance (i.e. friction) of the object upon which the separating force is being applied. Put differently, the components of the mouthpiece 100, in these embodiments, are so tightly fixed as to be adjusted only by a directed applied force and not by accidental force.

Figures 6A, 6B:
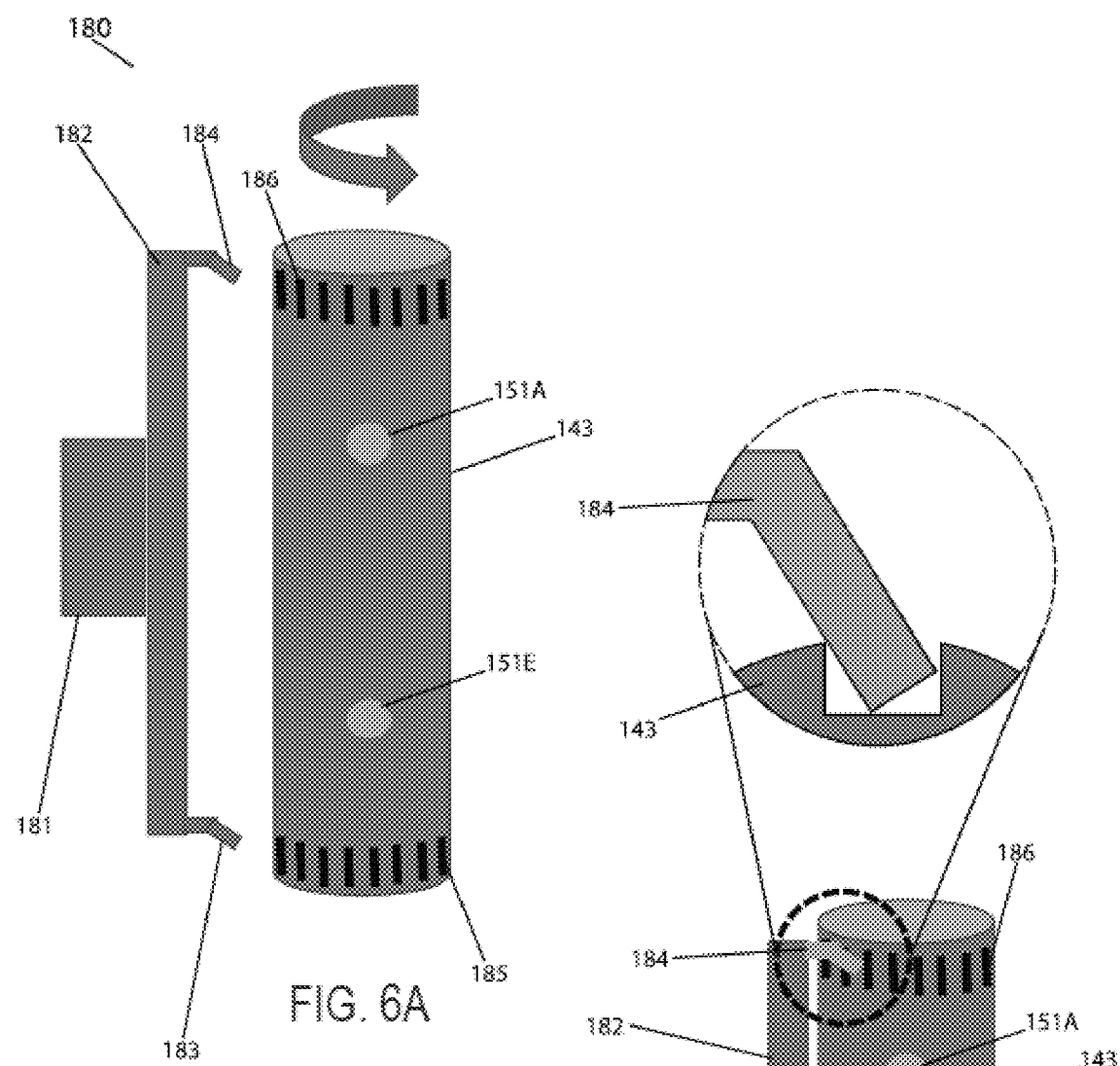
FIG. 6A is an exploded view of a pillar mechanism of the mouthpiece of FIG. 1, according to an exemplary embodiment.
FIG. 6B is a perspective view of the pillar mechanism of FIG. 6A, according to an exemplary embodiment.

In another embodiment, the first pillar 143, the second pillar 142, and the plurality of pillar supports 141 are structured such that the first pillar 143 and the second pillar 142 are only capable of unhindered rotation in a single direction. This may be accomplished via a pillar mechanism 180. The pillar mechanism 180 is shown in greater detail in FIGS. 6A-B. Although FIGS. 6A-B only show the pillar mechanism 180 in relation to the first pillar 143, any disclosure herein should not be restricted to the first pillar 143 and should be read as equally applicable to the second pillar 142. As shown in FIG. 6A, the pillar mechanism 6A includes a mechanism bar 182, a release tab 181, an upper tab 184, and a lower tab 183. The mechanism bar 182 extends axially along the z-axis 10 and is substantially parallel to the first pillar 143. The mechanism bar 182 includes the upper tab 184 on one end and the lower tab 183 on the other end, relative to the z-axis 10. The release tab 181 extends perpendicularly from the mechanism bar 182.

The pillar mechanism 180 may be manipulated between an engaged mode and a disengaged mode. When the pillar mechanism 180 is in the engaged mode, the first pillar 143 is only able to rotate in a first direction, such that the first pillar 143 is prevented from rotating in a second direction. In the example embodiment shown in FIGS. 6A-B, the first direction is counter clock-wise around the z-axis 10, and the second direction is clock-wise around the z-axis 10. In other words, when the pillar mechanism is in the engaged mode, the first pillar 143 is only able to rotate in the direction indicated by the arrow in FIGS. 6A-B. When the pillar mechanism 180 is in the disengaged mode, the rotation ability of the first pillar 143 is not restricted such that the first pillar 143 can rotate in either the first direction or the second direction. However, regardless of the mode of the pillar mechanism 180, the first pillar 143 is restricted in lateral or longitudinal movement by the plurality of pillar supports 141.

The pillar mechanism 180 may be manipulated from the engaged mode to the disengaged mode via the release tab 181. By default (i.e., when the release tab 181 is not pressed), the pillar mechanism 180 is in the engaged mode due to a spring (not shown). In the engaged mode, the upper tab 184 and the lower tab 183 interact with a plurality of grooves on the first pillar 143. This interaction is shown (for the upper tab 184) in the blown-up portion of FIG. 6B. When the release tab 181 is pressed, the upper tab 184 and the lower tab 183 move perpendicularly away from the first pillar 143 such that the upper tab 184 and the lower tab 183 no longer interact with the plurality of grooves in the first pillar 143.

In certain embodiments, the gum supports 111-114 and the gum ends 115-118 are manipulated and adjusted until in the desired position, at which point the first pillar 143 and the second pillar 142 are rotated in the first direction until the plurality of sanitary caps 119 are snugly fit on the object (e.g., gums of a human patient). Then, due to the restrictions placed by the pillar mechanism 180, the first pillar 143 and the second pillar 142 are held in place, and the fit of the sanitary caps 119 on the object remains snug. Once the related activity is completed (e.g., the separating force is no longer desired), the release tab 181 is pressed and the first pillar 143 and the second pillar 142 are free to rotate, thereby releasing the snug fit of the plurality of sanitary caps on the object.

As utilized herein with respect to numerical ranges, the terms "approximately," "about," "substantially," and similar terms generally mean+/−10% of the disclosed values unless otherwise specified. When the terms "approximately," "about," "substantially," and similar terms are applied to a structural feature (e.g., to describe its shape, size, orientation, direction, etc.), these terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the apparatus as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed:

1. An apparatus comprising:
    an outer portion comprising a first side, a second side, and a lower portion, wherein the lower portion spans between the first side and the second side;
    a pillar coupled to the first side and configured to rotate about a first axis, the pillar oriented along the first axis such that a longest dimension of the of the pillar extends along the first axis;
    a gum support coupled to the pillar and configured to rotate about a second axis that is perpendicular to the first axis; and
    a pillar mechanism coupled to the pillar, the pillar mechanism operable between a disengaged mode, in which the pillar is able rotate in a first direction about the first axis and a second direction about the first axis opposite of the first direction, and an engaged mode, in which the pillar is able to rotate in the first direction and not able to rotate in the second direction.

2. The apparatus of claim 1, wherein:
    the pillar comprises a plurality of grooves; and
    the pillar mechanism comprises:
        a mechanism bar substantially parallel to the pillar, the mechanism bar comprising a first end and a second end opposite of the first end,
        an upper tab coupled to the first end, the upper tab configured to interact with at least a first groove of the plurality of grooves when the pillar mechanism operates in the engaged mode, and
        a lower tab coupled to the second end, the lower tab configured to interact with at least a second groove of the plurality of grooves when the pillar mechanism operates in the engaged mode.

3. The apparatus of claim 1, wherein:
    the pillar is a first pillar;
    the apparatus further comprises a second pillar coupled to the second side and configured to rotate about a third axis, the third axis being parallel to the first axis;
    the outer portion further comprises an upper portion opposite of the lower portion; and
    the longest dimension of the pillar extends in a direction extending from the lower portion to the upper portion.

4. The apparatus of claim 3, wherein:
    the gum support is a first gum support; and
    the apparatus further comprises a second gum support coupled to the second pillar and configured to rotate about a fourth axis that is perpendicular to the third axis.

5. The apparatus of claim 1, wherein the second axis intersects the first axis.

6. The apparatus of claim 1, wherein:
    the gum support is an upper gum support; and
    the apparatus further comprises a lower gum support coupled to the pillar and configured to rotate about a third axis that is perpendicular to the first axis, the lower gum support disposed below the upper gum support.

7. The apparatus of claim 1, further comprising a sanitary cap coupled to an end of the gum support.

8. A method of opening a mouth using a mouthpiece, the method comprising:
    inserting an upper gum end into the mouth, wherein the upper gum end is received by an upper portion of the mouth;
    applying a separating force to an upper gum support coupled to the upper gum end, the upper gum support coupled to a pillar, an entirety of the pillar configured to rotate about a single axis, the upper gum support configured to rotate about a second axis that is perpendicular to the single axis;
    inserting a lower gum end into the mouth, wherein the lower gum end is received by a lower portion of the mouth;
    applying the separating force to a lower gum support coupled to the lower gum end, the lower gum support coupled to the pillar; and
    limiting rotation of the pillar such that the pillar is able to rotate in a first direction about the single axis and not able to rotate in a second direction about the single axis opposite of the first direction.

9. The method of claim 8, wherein:
    the lower gum support is configured to rotate about a third axis that is perpendicular to the single axis; and applying the separating force to the upper gum support and the lower gum support causes the upper gum end and the lower gum end to move away from each other.

10. The method of claim 8, further comprising:
inserting an inner wedge into the mouth, wherein an upper surface of the inner wedge is received by the upper portion of the mouth;
inserting a laryngoscope into the inner wedge; and
inserting a breathing tube into the inner wedge.

11. The method of claim 10, further comprising removing the laryngoscope from the inner wedge.

12. The method of claim 8, wherein:
the upper gum end is a first upper gum end;
the upper gum support is a first upper gum support;
the pillar is a first pillar; and
the method further comprises:
    inserting a second upper gum end into the mouth, wherein the second upper gum end is received by the upper portion of the mouth, and
    applying the separating force to a second upper gum support coupled to the second upper gum end, the second upper gum support coupled to a second pillar.

13. The method of claim 12, wherein:
the second pillar is configured to rotate about a third axis; and
the second upper gum support is configured to rotate about a fourth axis that is perpendicular to the third axis.

14. The method of claim 8, wherein the pillar is received by a pillar support such that the pillar may rotate about the single axis within the pillar support.

15. The method of claim 8, wherein the mouthpiece further comprises a sanitary cap configured to receive the upper gum end.

16. An apparatus comprising:
an outer portion comprising a first outer side surface, a second outer side surface, an outer lower surface spanning between the first outer side surface and the second outer side surface, and an outer upper surface, the first outer side surface, the second outer side surface, and the outer lower surface at least partially defining an outer primary opening, the outer upper surface defining an outer secondary opening having a width less than a width of the outer primary opening, the outer portion configured to be positioned outside of a mouth;
an inner wedge comprising a first inner side surface, a second inner side surface, an inner lower surface spanning between the first inner side surface and the second inner side surface, and an inner upper surface, the inner wedge positioned within the outer primary opening of the outer portion, the first inner side surface, the second inner side surface, and the inner lower surface at least partially defining an inner primary opening, the inner upper surface defining an inner secondary opening having a width less than a width of the inner primary opening, the width of the inner secondary opening being equal to the width of the outer secondary opening, the inner wedge configured to be at least partially inserted into the mouth;
a first upper gum end coupled to the outer portion and configured to be received by an upper portion of the mouth; and
a first lower gum end coupled to the outer portion and configured to be received by a lower portion of the mouth.

17. The apparatus of claim 16, further comprising:
a first upper gum support coupled to the first upper gum end;
a second upper gum support coupled to a second upper gum end;
a first lower gum support coupled to the first lower gum end; and
a second lower gum support coupled to a second lower gum end.

18. The apparatus of claim 16, further comprising:
a first sanitary cap configured to receive the first upper gum end;
a second sanitary cap configured to receive a second upper gum end;
a third sanitary cap configured to receive the first lower gum end; and
a fourth sanitary cap configured to receive a second lower gum end.

19. The apparatus of claim 16, wherein a first width of the first inner side surface proximate the inner lower surface is greater than a second width of the first inner side surface proximate the inner upper surface.

20. The apparatus of claim 16 further comprising:
a second upper gum end coupled to the outer portion and configured to be received by the upper portion of the mouth;
a second lower gum end coupled to the outer portion and configured to be received by the lower portion of the mouth;
a first pillar rotatably coupled to the outer portion and coupled to the first upper gum end and the first lower gum end; and
a second pillar rotatably coupled to the outer portion and coupled to the second upper gum end and the second lower gum end.

* * * * *